United States Patent
Girijavallabhan et al.

[11] Patent Number: 5,795,874
[45] Date of Patent: Aug. 18, 1998

[54] WATER SOLUBLE ANTIBIOTICS

[75] Inventors: Viyyoor M. Girijavallabhan, Parsippany; Anil K. Saksena, Upper Montclair; Frank Bennett, Piscataway; Edwin Jao, Warren; Naginbhai M. Patel, Piscataway; Ashit Ganguly, Upper Montclair, all of N.J.

[73] Assignee: Schering Corporation, Kenilworth, N.J.

[21] Appl. No.: 770,469

[22] Filed: Dec. 20, 1996

Related U.S. Application Data

[63] Continuation of Ser. No. 577,656, Dec. 22, 1995, Pat. No. 5,652,226.
[51] Int. Cl.[6] ............... A81K 31/72; C07H 15/24
[52] U.S. Cl. ............... 514/54; 536/16.8; 536/18.1; 514/35; 514/456
[58] Field of Search ............... 536/16.8, 18.1; 514/54, 25, 456

[56] References Cited

U.S. PATENT DOCUMENTS

| | | | |
|---|---|---|---|
| 4,597,968 | 7/1986 | Waitz et al. | 424/118 |
| 4,622,314 | 11/1986 | Ganguly | 514/54 |
| 4,767,748 | 7/1986 | Ganguly et al. | 514/54 |
| 5,627,165 | 5/1997 | Glazier | 514/75 |

FOREIGN PATENT DOCUMENTS

WO 87/02366  4/1987  WIPO.

OTHER PUBLICATIONS

Bundgaard, H.: Design of Prodrugs : Bioreversible Derivatives for Various Functional Groups and Chemical Entitled in Designing of Prodrugs Edited by Hans Bundgaard Elsevier, 1985.

Kirk–Othmer, Encyclopedia of Chemical Technology, 4th Edition, 1992, vol. 3, Antibiotics (Oligosaccharides) pp. 259–266.

*Primary Examiner*—C. Warren Ivy
*Assistant Examiner*—Charanjit S. Aulakh
*Attorney, Agent, or Firm*—Joseph T. Majka; Thomas D. Hoffman

[57] ABSTRACT

The compound of the formula I

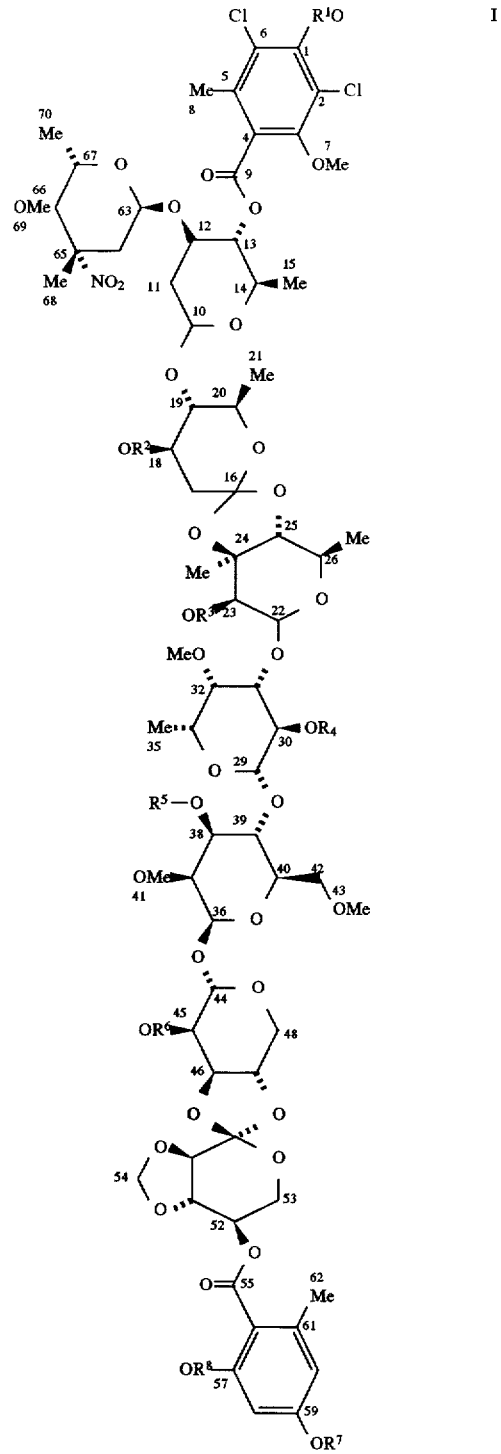

wherein $R^1$, $R^2$, $R^3$, $R^4$, $R^5$, $R^6$, $R^7$, and $R^8$ are as defined herein, are described. These compounds are antibacterial agents.

6 Claims, No Drawings

WATER SOLUBLE ANTIBIOTICS

The present application is a continuation of U.S. Pat. Ser. No. 08/577,656 filed Dec. 22, 1995 now U.S. Pat. No. 5,652,226, the benefit of which application is claimed pursuant to the provisions of 35 USC 120.

BRIEF SUMMARY OF THE INVENTION

The invention relates to compounds of the formula I

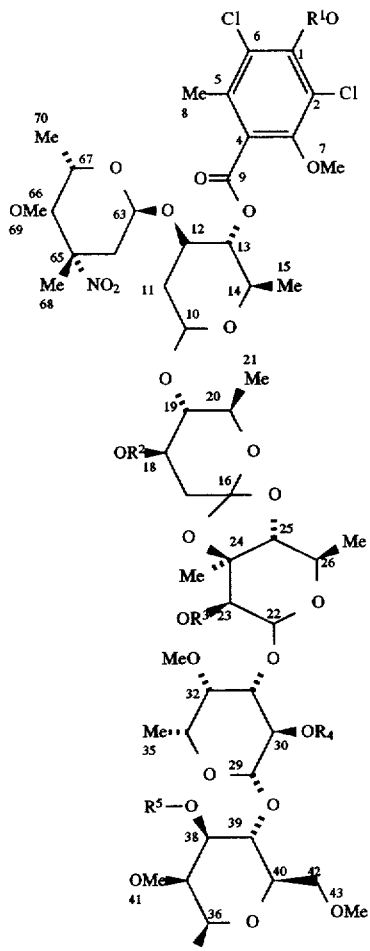

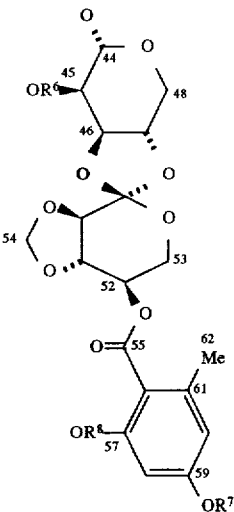

wherein one to seven of $R^1$, $R^2$, $R^3$, $R^4$, $R^5$, $R^6$, $R^7$, and $R^8$ are hydrogen and the remaining $R^1$, $R^2$, $R^3$, $R^4$, $R^5$, $R^6$, $R^7$, and $R^8$ are groups convertible in vivo into hydrogen.

Preferred are compounds of the formula I'

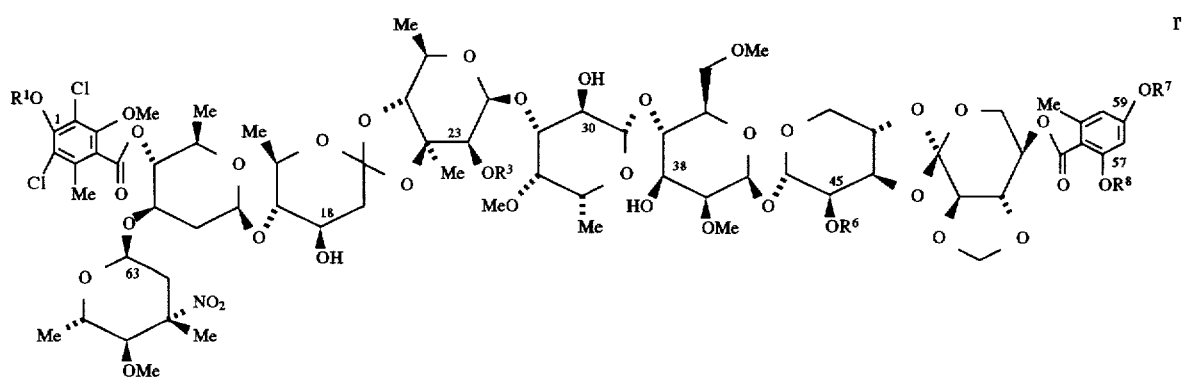

wherein one to four of $R^1$, $R^3$, $R^6$, $R^7$, and $R^8$ are hydrogen and the remaining $R^1$, $R^3$, $R^6$, $R^7$, and $R^8$ are groups convertible in vivo to hydrogen.

Preferred are compounds of the formula

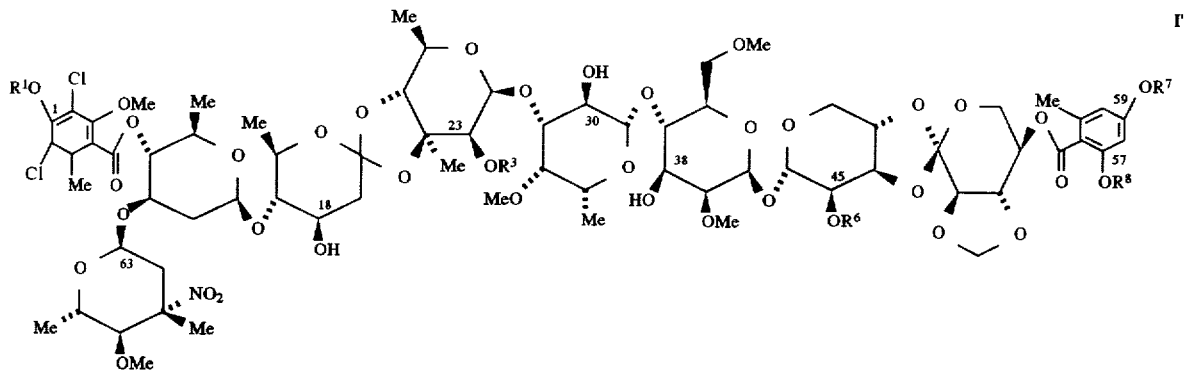

wherein one to four of $R^1$, $R^3$, $R^6$, $R^7$, and $R^8$ are hydrogen and the remaining $R^1$, $R^3$, $R^6$, $R^7$, and $R^8$ are each independently selected from the group consisting of

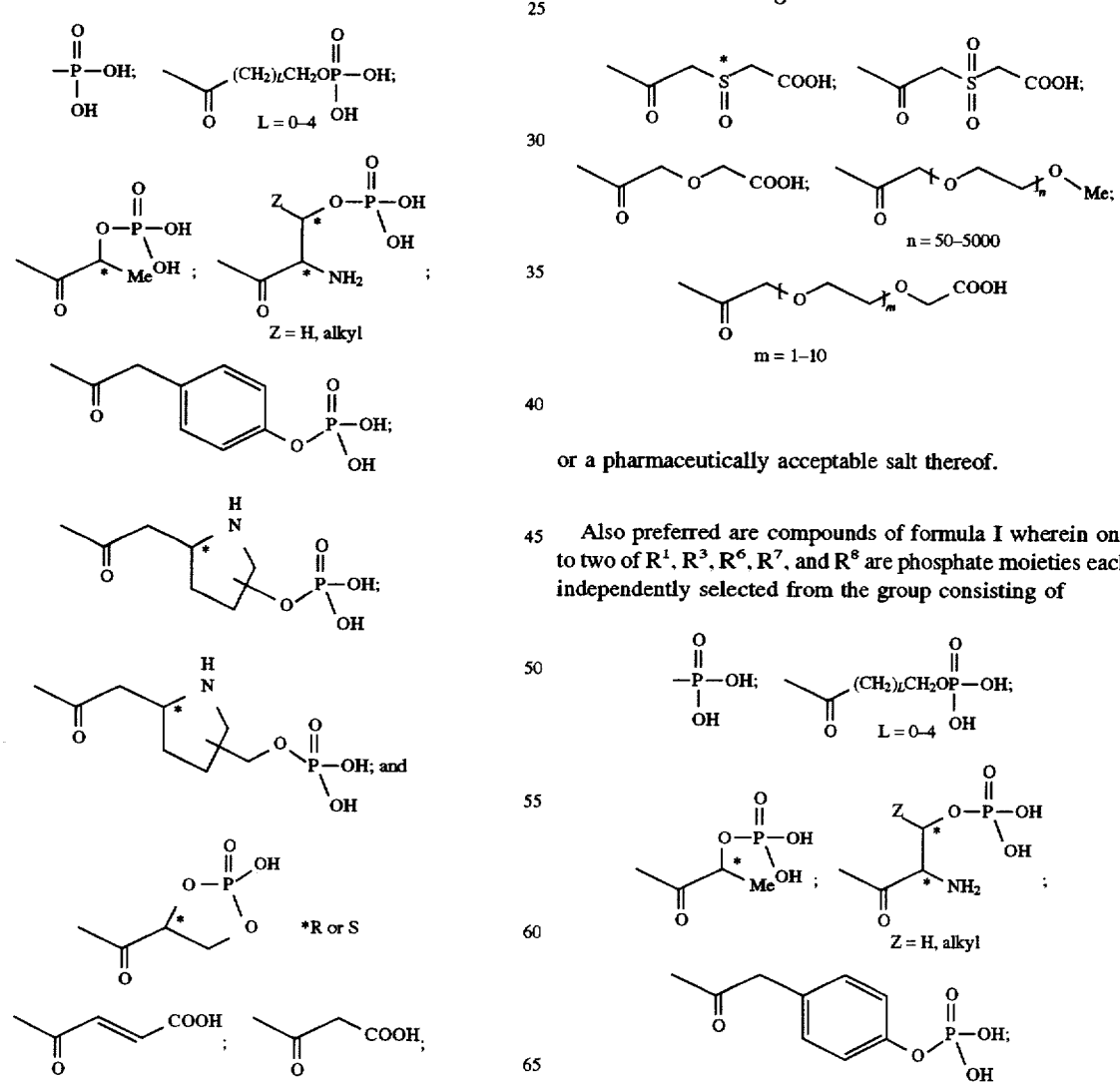

or a pharmaceutically acceptable salt thereof.

Also preferred are compounds of formula I wherein one to two of $R^1$, $R^3$, $R^6$, $R^7$, and $R^8$ are phosphate moieties each independently selected from the group consisting of -continued

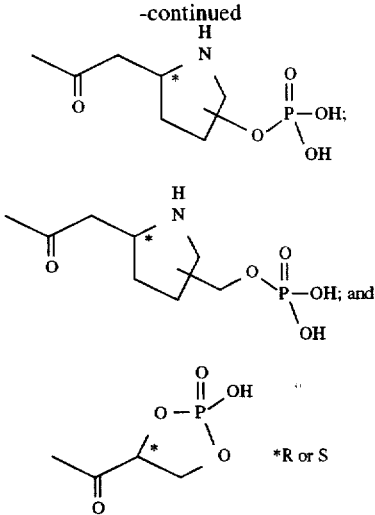

or a pharmaceutically acceptable salt thereof.

Also preferred are compounds of formula I wherein one to four of $R^1$, $R^3$, $R^6$, $R^7$, and $R^8$ are diacid monoester moieties each independently selected from the group consisting of

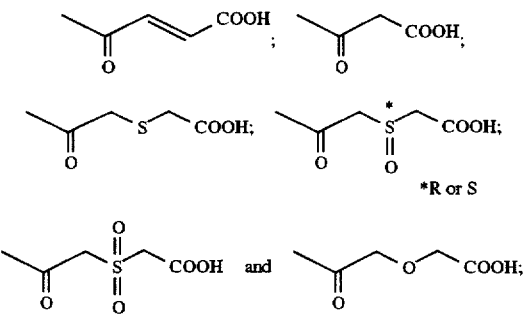

or a pharmaceutically acceptable salt thereof

Also preferred are compounds of formula I wherein one to four of $R^1$, $R^3$, $R^6$, $R^7$, and $R^8$ are polyether esters each independently selected from the group consisting of

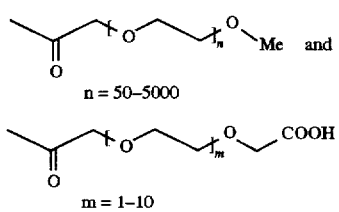

or a pharmaceutically acceptable salt thereof.

Also preferred are compounds of formula I wherein one to four of $R^1$, $R^3$, $R^6$, $R^7$, and $R^8$ are

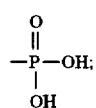

or a pharmaceutically acceptable salt thereof.

The preferred phosphate esters of the invention are compounds of formula I' wherein $R^7$ is

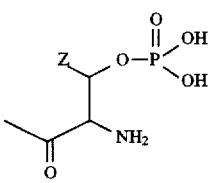

and Z is methyl

The compounds of this invention contain groups convertible in vivo into hydrogen which may contain a chiral center. This invention includes compounds which may exist as each enantiomer whose chiral center is designated as having the R or S absolute configuration. Equimolar and non-equimolar mixtures of such enantiomers are included also within the scope of this invention.

Also preferred are compounds of formula I wherein one to four of $R^1$, $R^3$, $R^6$, $R^7$, and $R^8$ are

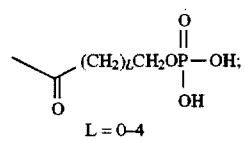

or a pharmaceutically acceptable salt thereof.

Also preferred are compounds of formula I wherein one to four of $R^1$, $R^3$, $R^6$, $R^7$, and $R^8$ are

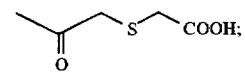

Also preferred are compounds of formula I wherein one to four of $R^1$, $R^3$, $R^6$, $R^7$, and $R^8$ are Also preferred are compounds of formula I wherein one to four of $R^1$, $R^3$, $R^6$, $R^7$, and $R^8$ are Also preferred are compounds of formula I wherein one to four of $R^1$, $R^3$, $R^6$, $R^7$, and $R^8$ are or a pharmaceutically acceptable salt thereof.

Also preferred is the compound of formula Ia

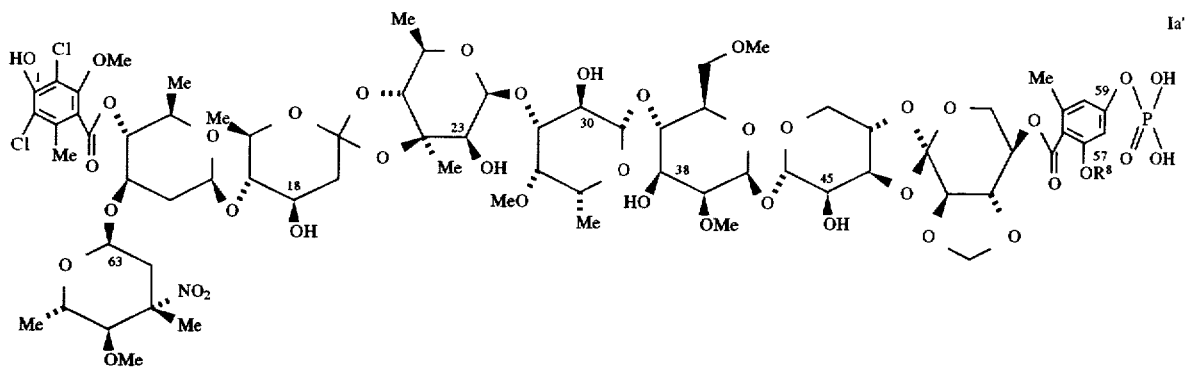

or a pharmaceutically acceptable salt thereof.

Most preferred is the compound of the formula

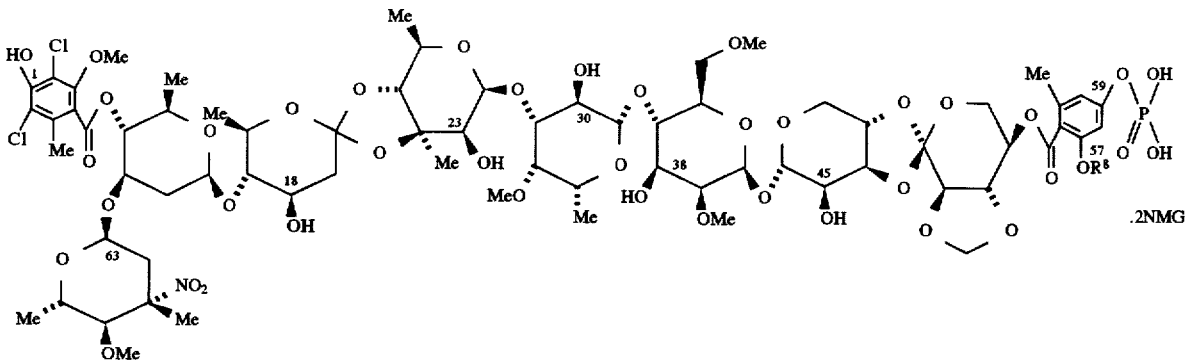

The invention also relates to pharmaceutical compositions comprising a compound of formula I and a pharmaceutically acceptable carrier material.

The invention also relates to a method for treating and/or preventing bacterial infections in a mammal afflicted with the same which comprises administering an antibacterial effective amount of a compound of formula I or a pharmaceutically acceptable salt thereof. Preferred methods for treating and/or preventing bacterial infections are those wherein the mode of administration is intravenous or intramuscular.

DETAILED DESCRIPTION OF THE INVENTION

As used herein, the term alkyl" means straight or branched-chain alkyl groups of one to ten carbon atoms; straight or branched-chain alkyl groups of one to six carbon atoms are preferred.

SCHEME I
Preparation of C-59 Aryl Phosphate:
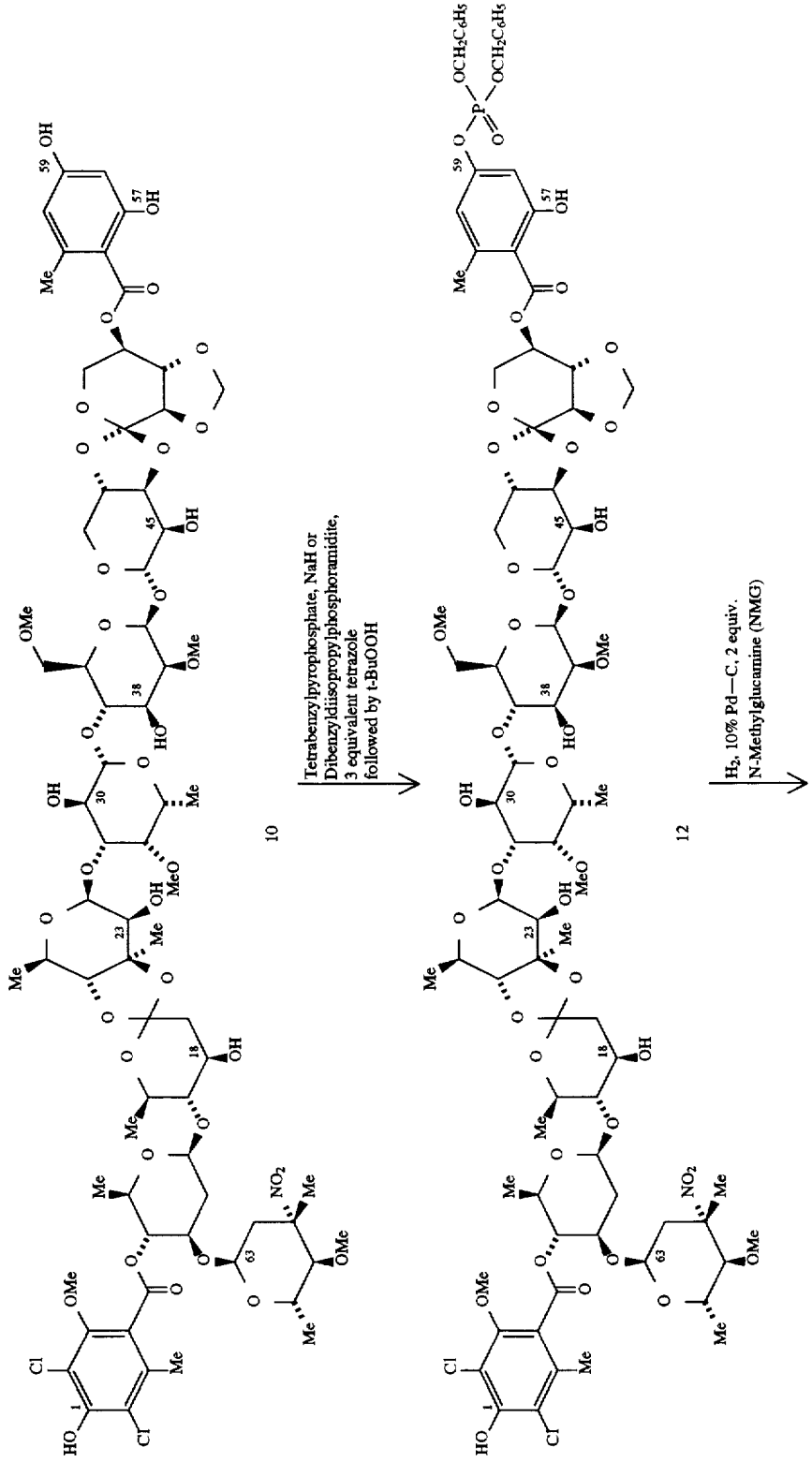

-continued
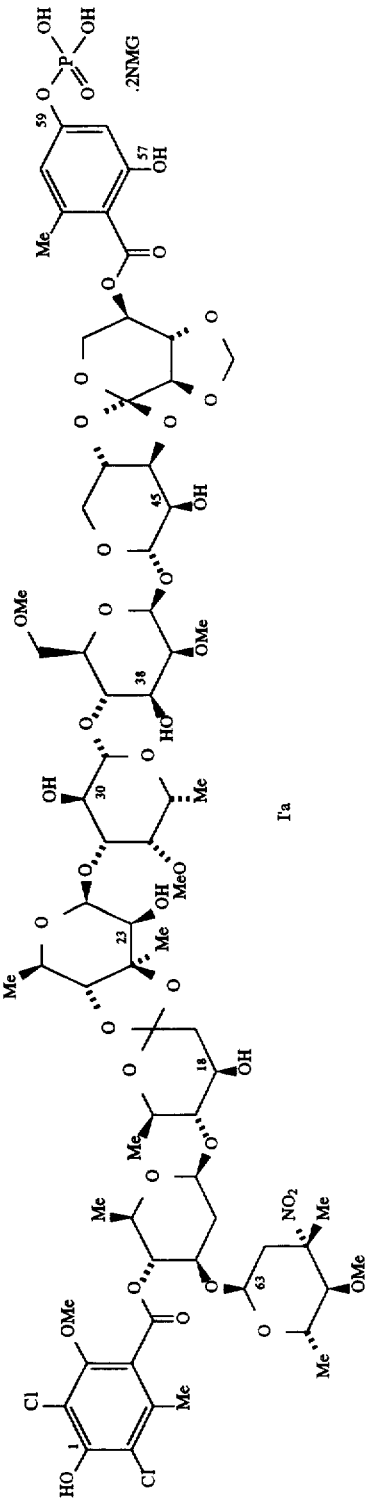
I'a
SCHEME II
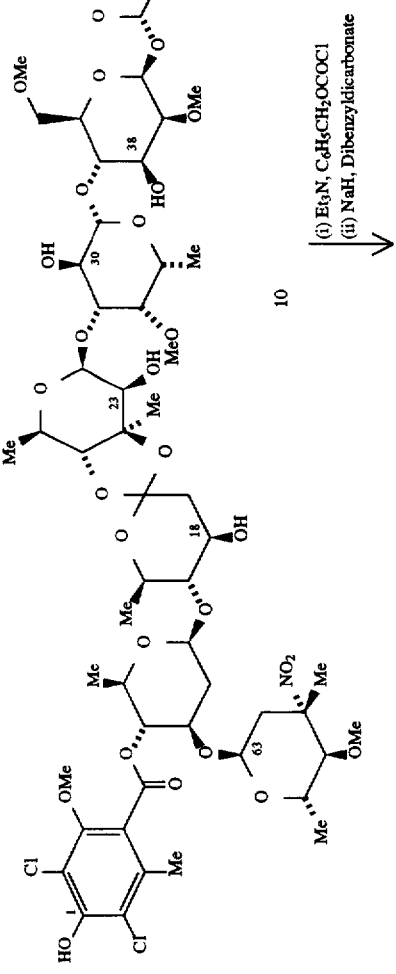
10
$\Bigg\downarrow$ (i) Et₃N, C₆H₅CH₂OCOCl
(ii) NaH, Dibenzyldicarbonate
Preparation of C-1 Monoaryl Phosphate:

-continued
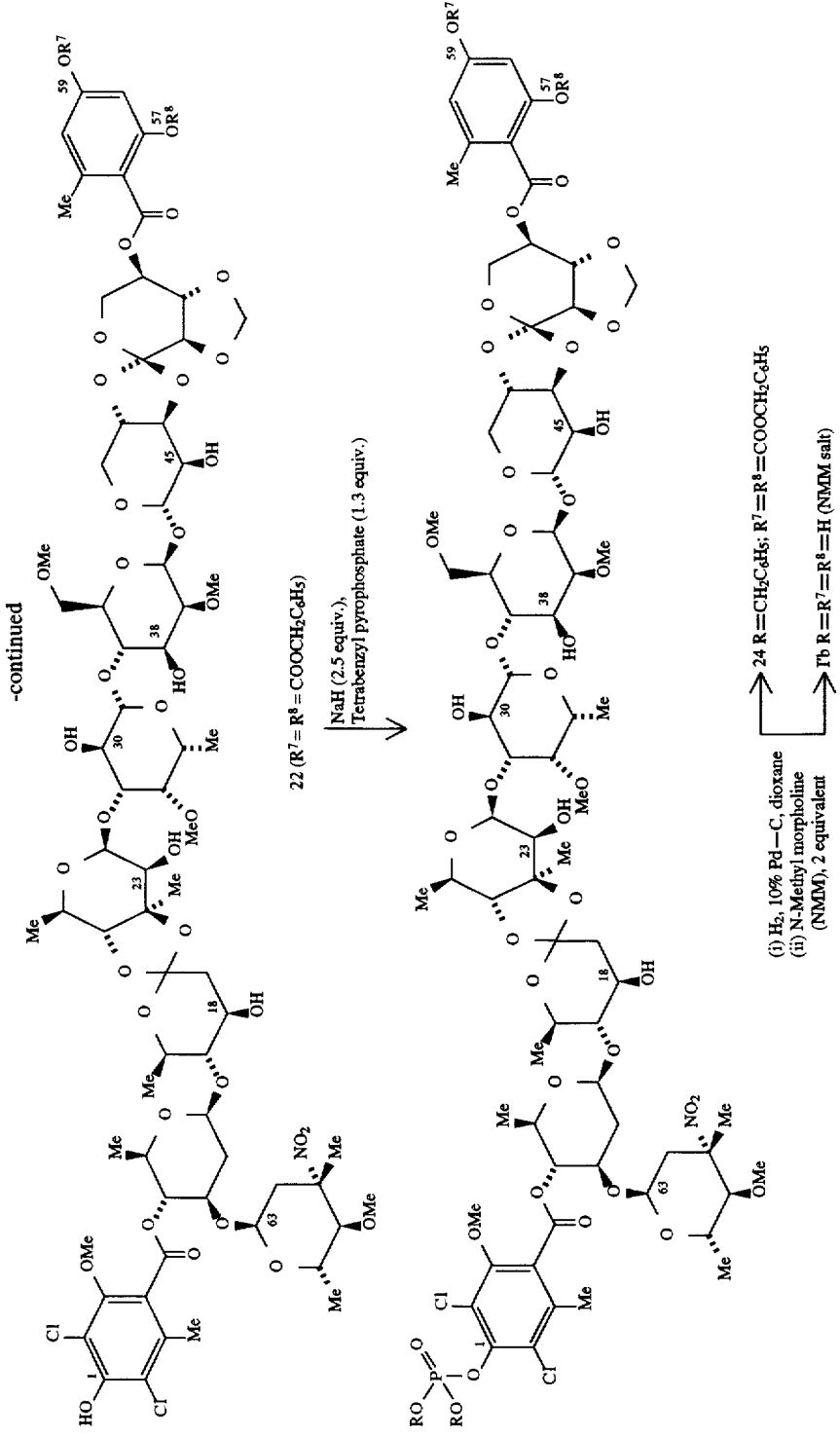

Preparation of C-1 and C-59 Butyrate-Phosphates:
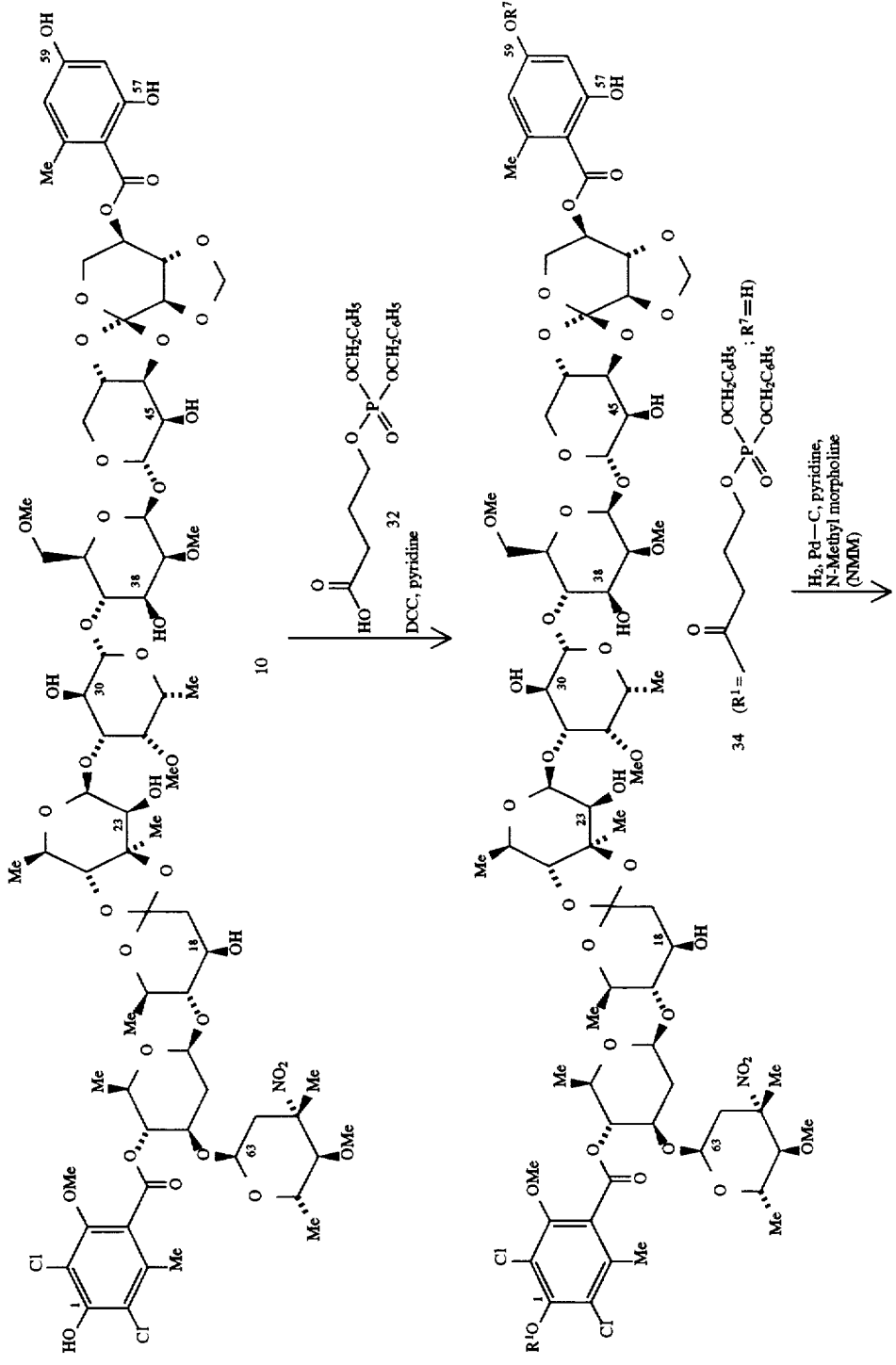

-continued
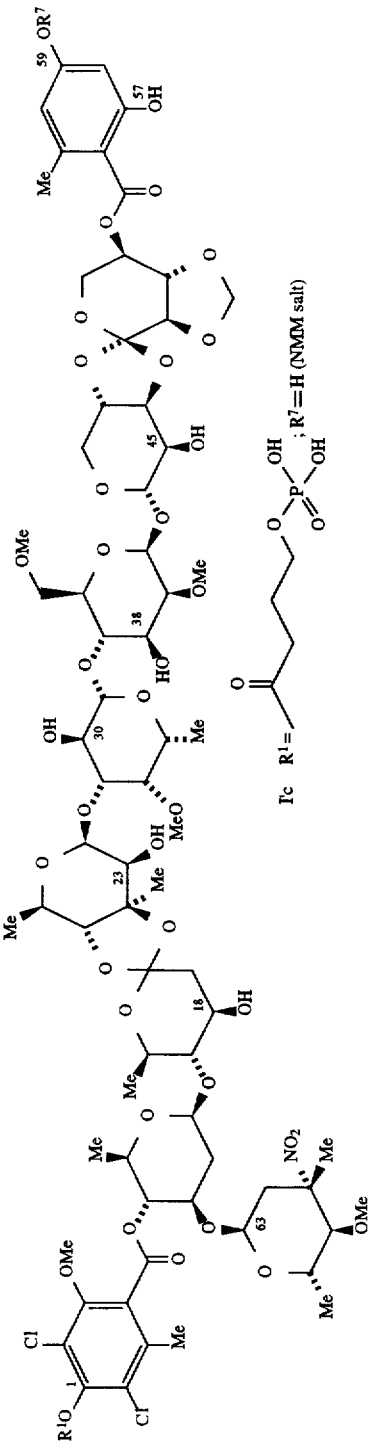
SCHEME IIIB
Preparation of C-1 and C-59 Butyrate-Phosphates:
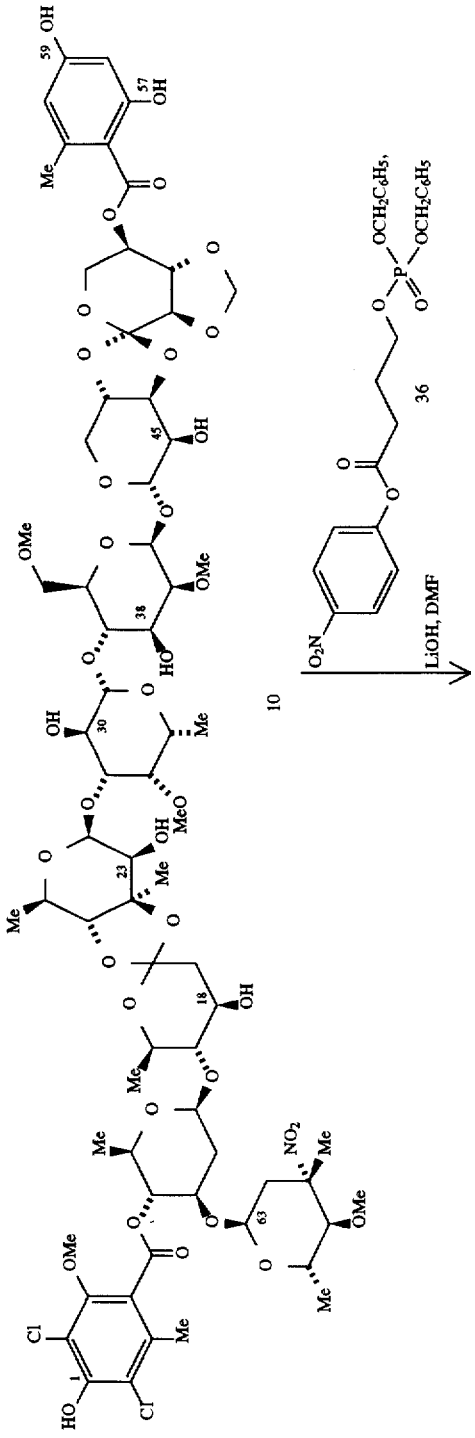

-continued
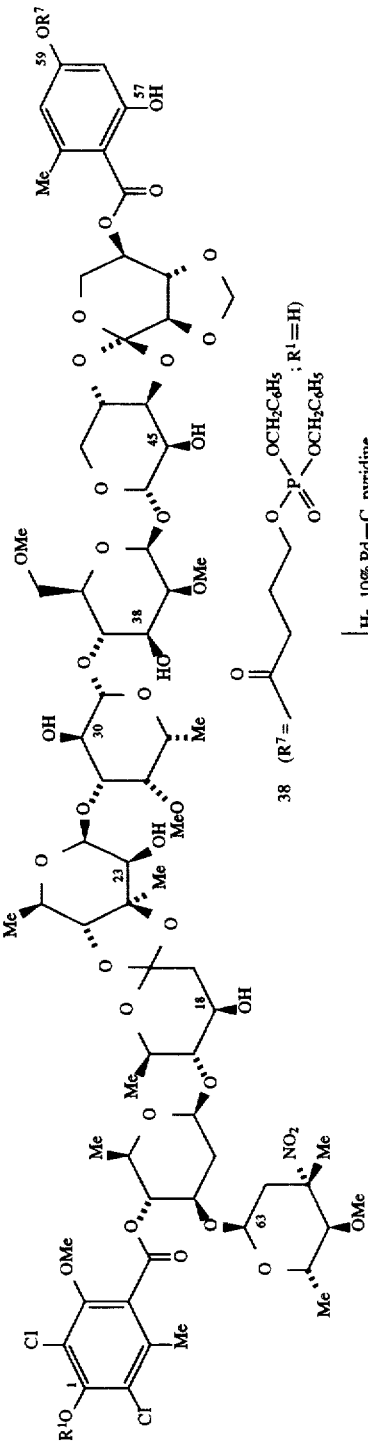
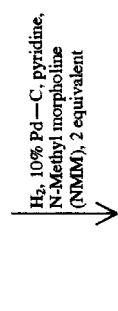
38 (R⁷= ; R¹=H)
H₂, 10% Pd—C, pyridine, N-Methyl morpholine (NMM), 2 equivalent
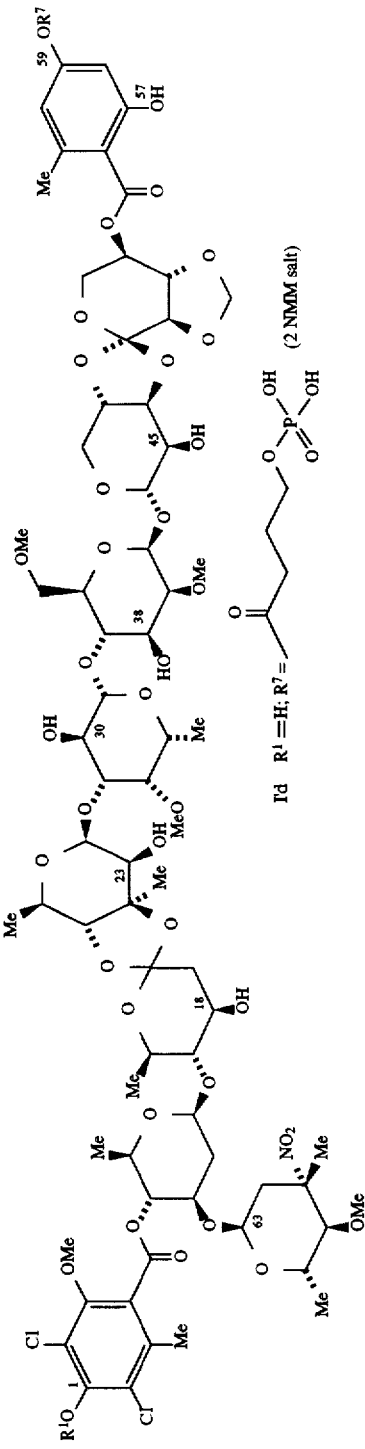
Id R¹=H; R⁷= (2 NMM salt)
SCHEME IVA
Preparation of fumaric acid monoesters:
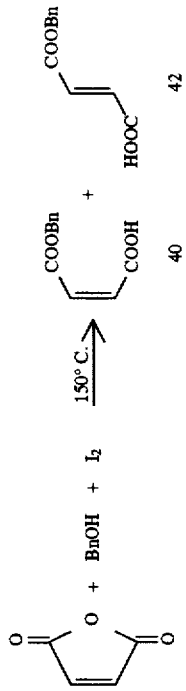

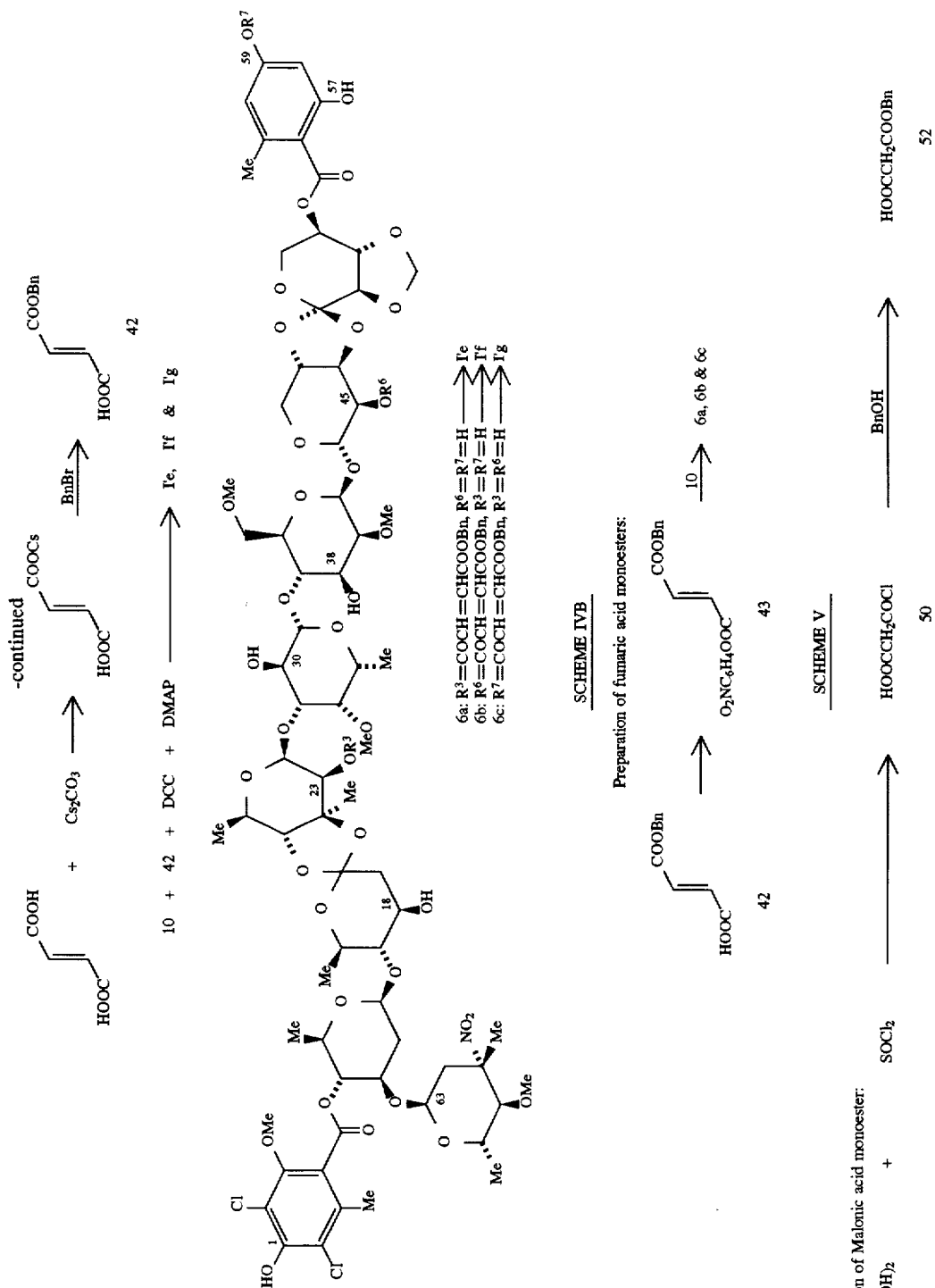

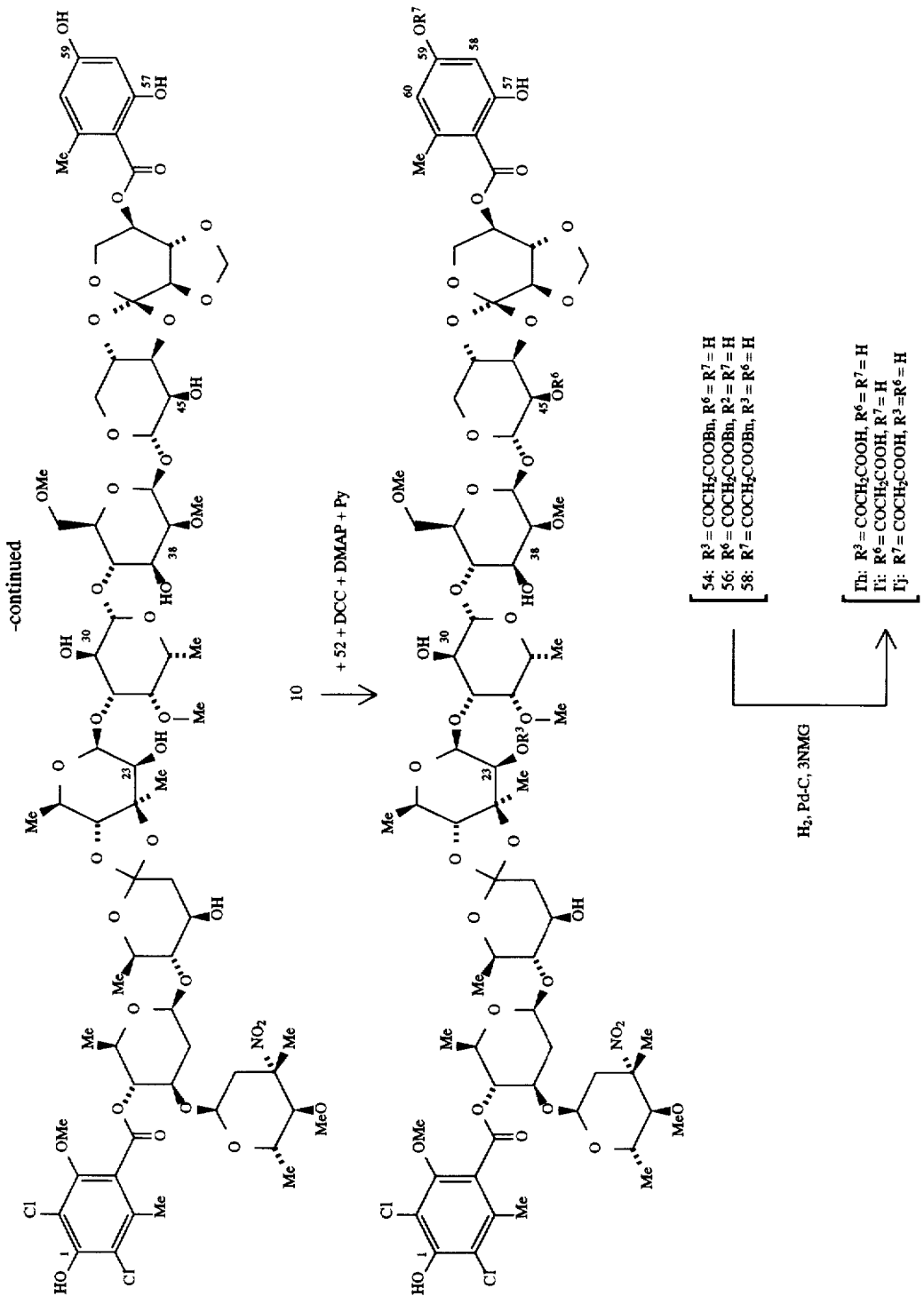

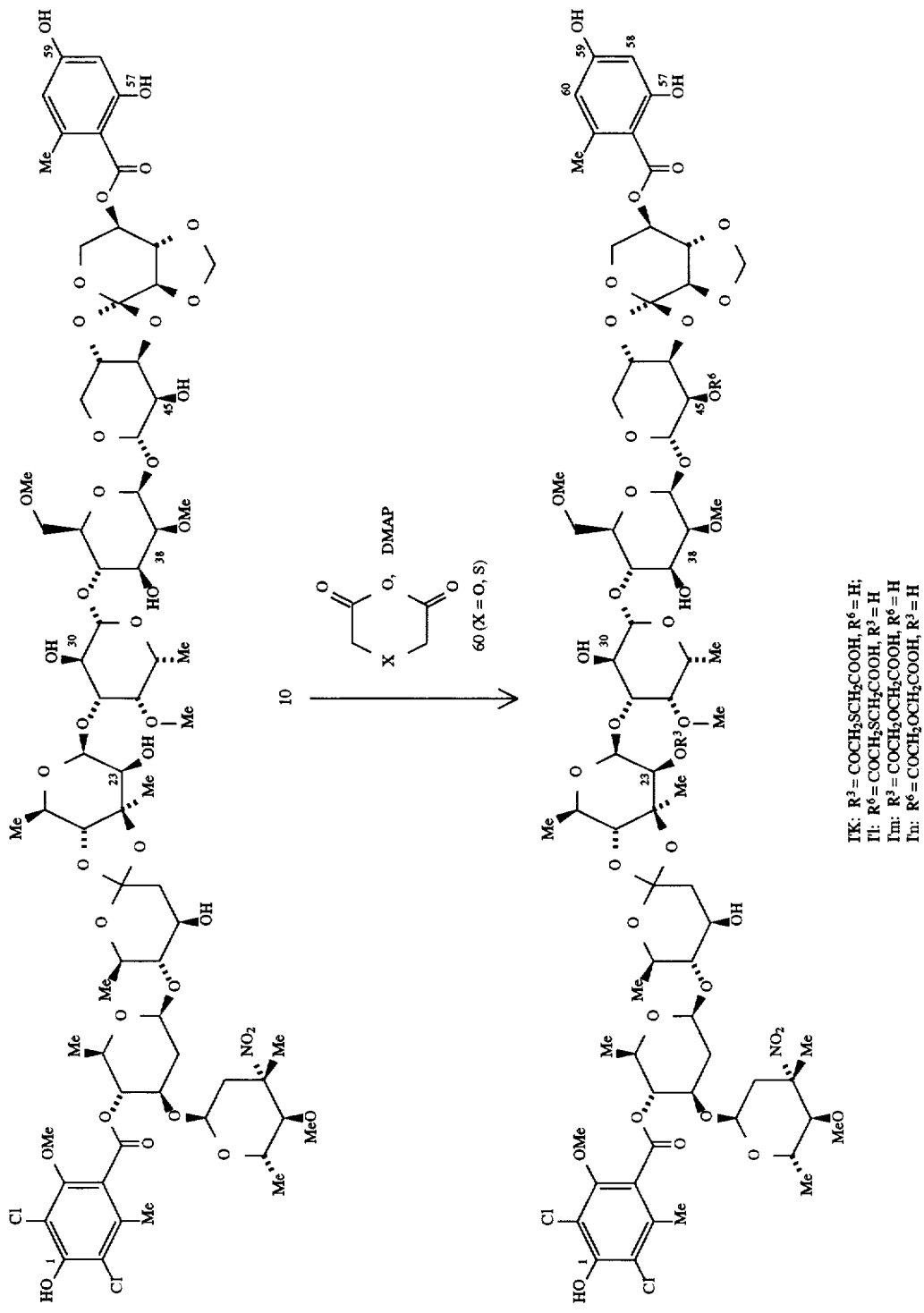

-continued
SCHEME VII
Preparation of polyether esters:
A. $CH_3(OCH_2CH_2)_nOH$
$$\xrightarrow{ClCH_2COONa, NaH, THF} CH_3(OCH_2CH_2)_nOCH_2COOH$$
$$70 \qquad \qquad 72$$
B.
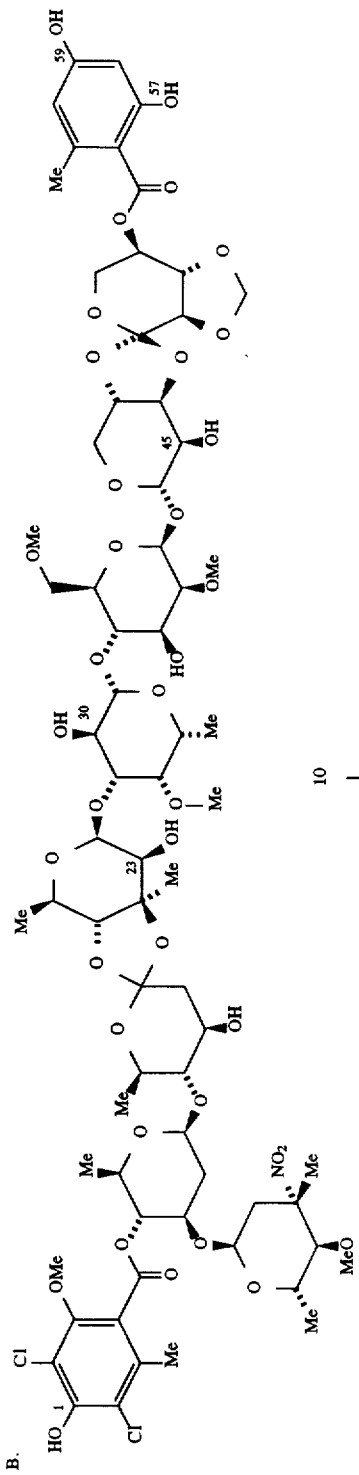
$$10 \xrightarrow{72, DCCD, DMAP, CH_2Cl_2}$$
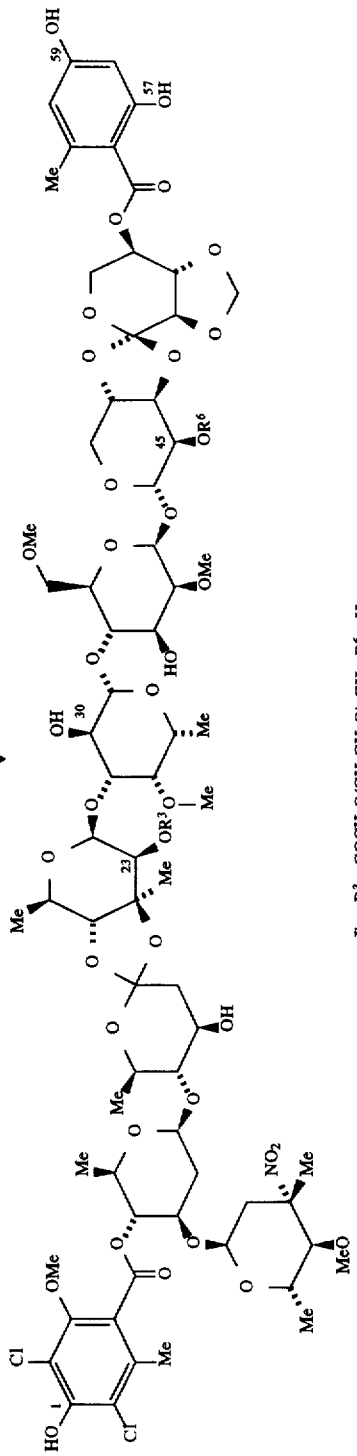
Io: $R^3 = COCH_2O(CH_2CH_2O)_nCH_3$, $R^6 = H$
Ip: $R^3 = COCH_2O(CH_2CH_2O)_nCH_3$, $R^3 = H$ Scheme I provides a procedure for preparation of phosphates of compounds of formula I' (i.e., I'a wherein $R^7=PO_3H_2$ and $R^1=R^3=R^6=R^8=H$). The reaction of everninomicin (10) and 10 equivalents of NaH and 1.5 equivalents of tetrabenzyl-pyrophosphate in tetrahydrofuran ("THF") at room temperature for 2½ hours gave dibenzyl phosphosphate ester 12 after silica gel chromatography using 5% methanol in methylene chloride as an eluent. In an alternative procedure for preparation of 12, one equivalent of 10 was treated with 1.5 to 3 equivalents of N,N'-dibenzyldiisopropylphosphoramidite and 3–6 equivalents of tetrazole in methylene chloride and the resulting mixture was stirred for 3 hours. Three to six equivalents of tert-butyl hydroperoxide (as a 5.5 molar solution in iso-octane) were added and the resulting reaction mixture was stirred for an additional three hours. The crude product in ethylacetate (EtOAc) was washed with sodium thiosulfate and purified using silica gel chromatography to give the dibenzyl phosphate 12. Treatment of 12 in pyridine with 10% Pd/C under a hydrogen atmosphere for 5 to 7 hours at room temperature in the presence of 2 equivalents of N-methylglucamine (NMG) gave I'a.2NMG salt. In an alternate procedure, 12 may be treated with 10% Pd/C under a hydrogen atmosphere in an aprotic solvent, e.g. dioxane, at room temperature for about 5 to 7 hours to give I'a.

Scheme II provides a procedure for the preparation of phosphates of the compounds of formula I' (i.e. I'b wherein $R^1=PO_3H_2$, and $R^3=R^6=R^7=R^8=H$.) Treatment of 10 with one equivalent of benzylchloroformate and base, e.g., triethylamine (Et$_3$N) in methylene chloride at room temperature for two hours gave a mixture of dibenzylcarbonate 22 as well as the monobenzylcarbonate (not shown). The monocarbonate was then converted into the dicarbonate 22 using dibenzylcarbonate and sodium hydride (NaH) as a base. Separation of the crude reaction mixture on silica gel chromatography using methanol-methylene chloride as eluent gave pure 22. Treatment of 22 with 2.5 equivalents of NaH at −10° C. in dry THF gave the corresponding sodium salt. Addition of 1.3 equivalents of tetrabenzylpyrophosphate to the stirred reaction mixture of the sodium salt of 22 at −10° C. for 2 hours gave a reaction mixture which was stirred overnight at 0° C. A standard workup of the so-formed reaction mixture and silica gel column chromatography of the crude product gave 24. Treatment of 24 in pyridine with 10% Pd/C under a hydrogen atmosphere overnight at room temperature gave the pyridine salt of phosphate I'b. Treatment of the pyridine salt of I'b with two equivalents of base, e.g., N-methylmorpholine (NMM), gave I'b.2NMM salt.

Scheme IIIA provides a procedure for preparation of butyrate phosphates of the compounds of formula I' (i.e., I'c wherein $R_1=CO(CH_2)_3OPO_3H_2$ and $R^3=R^6=R^7=R^8=H$.) the compound 32 may be prepared by reaction of 4-bromobutanoyl bromide with 2,2,2-trichloroethanol to produce the corresponding trichloroethyl ester. Treatment of the so-formed ester with 1.5 equivalents of silver dibenzyl phosphate (available from Sigma Chemical Co., St. Louis) in an aprotic solvent at elevated temperature overnight gave (after a standard workup) the trichloroethyl ester of 32. Removal of the trichloroethyl ester group may be accomplished by use of zinc in acetic acid-THF to give the dibenzyl phosphate of acid 32. Treatment of 10 with 1 equivalent of dibenzyl phosphate of acid 32 in methylene chloride with 1.3–1.5 equivalents of dicyclohexylcarbodiimide ("DCC") and base, e.g., pyridine, at room temperature overnight gave dibenzyl butyrate phosphate 34. Treatment of 34 with 10% Pd/C in dioxane containing 2 equivalents of NMM under a hydrogen atmosphere gave I'c. Treatment of I'c with 2 to 4 equivalents of base, e.g., NMM, gave the corresponding amine salts, i.e., I'c.4NMM salt.

Scheme IIIb provides a procedure for preparation of butyrate phosphates of compounds of formula I'. i.e. I'd wherein $R^7=CO(CH_2)_3OPO_3H_2$ and, $R^1=R^3=R^6=R^8=H$. Compound 36 may be prepared by reaction of p-nitrophenol with the acid halide of 32. Treatment of 10 with 1 equivalent of the diester 36 in DMF with 1.5 equivalents of lithium hydroxide monohydrate at room temperature overnight gave dibenzylbutyrate phosphate 38. Treatment of 38 with 10% Pd/C in dioxane with 2 equivalents of NMM under hydrogen atmosphere for 5 hours gave the amine salt of I'd. In an alternate procedure, 38, may be treated with 10% Pd/C in dioxane under a hydrogen atmosphere for five hours to give I'd. Treatment of I'd with two to four equivalents of base, e.g. NMM in dioxane gave the corresponding amine salts I'd 4NMM salt.

Scheme IVa provides a procedure for preparation of fumaric acid esters of the compounds of formula I', I'e, i.e. wherein

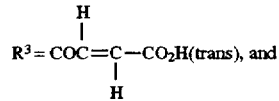

$R^1 = R^6 = R^7 = R^8 = H$; I'f wherein $R^6 = COC=C-CO_2H$(trans), and

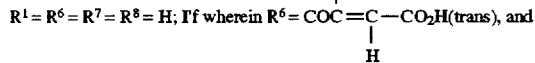

$R^1 = R^3 = R^7 = R^8 = H$; and

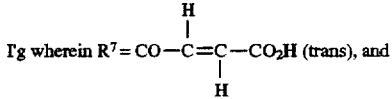

I'g wherein $R^7 = CO-C=C-CO_2H$ (trans), and

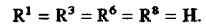

$R^1 = R^3 = R^6 = R^8 = H$.

Fumaric Acid is treated with cesium carbonate and benzyl bromide to give monobenzylester 42. Treatment of 10 with 1 equivalent of 42 in the presence of 1 equivalent of DCC and of the base, 4-(N,N-dimethylamino)pyridine ("DMAP") and 3 equivalents of NMM in methyline chloride at 0° C. gave a reaction mixture which was stirred overnight at room temperature to give a mixture of the benzyl esters of I'e, I'f and I'g. Treatment of the mixture of benzyl esters with 10% Pd/C in dioxane containing 2 equivalents of NMM gave a mixture of the amine salts of I'e, I'f and I'g. In an alternate procedure, treatment of the mixture of benzyl esters of I'e, I'f and I'g with 10% Pd/C in dioxane gave a crude mixture of I'e, I'f and I'g. Silica gel column chromatography of the crude mixture using 5% and 10% methanol in methylene chloride gave the pure fumaric monoesters I'e, I'f and I'g.

Scheme IVb provides an alternative procedure for preparation of the fumaric acid monoesters of the compounds of formula I'. i. e., I'e, I'f and I'g. The monobenzyl ester of fumaric acid 42 is converted into para-nitrophenyl ester 43 by treatment of 42 with 4-nitrophenol, DCC and DMAP. Treatment of 43 with 1 equivalent of 10 in the presence of triethyl amine in methylene chloride gives the mixture of benzyl esters of I'e, I'f and I'g. Treatment of the mixture by methods described in above regarding Scheme IVA gives pure I'e, I'f and I'g.

Scheme V provides a procedure for preparation of malonic acid monoesters of the compounds of formula I', i.e. I'h wherein $R^3=COCH_2CO_2H$ and $R^1=R^6=R^7=R^8=H$; I'i wherein $R^6=COCH_2CO_2H$ and $R^1=R^3=R^7=R^8=H$; and I'j, wherein $R^7=COCH_2CO_2H$, $R^1=R^3=R^6=R^8=H$. The monobenzyl ester 52 is prepared by treatment of malonic acid with thionyl chloride and benzyl alcohol. Treatment of 10 in methylene chloride with 1 equivalent of 52 and 1.3–1.5 equivalents of DCC and base, e.g. pyridine and DMAP gave a mixture of monobenyl esters 54, 56 and 58. Treatment of the mixture with 10% Pd/C in dioxane gave a mixture of malonic acid monoesters I'h, I'i and I'j. Separation of the mixture using silica gel chromatography gave the individual compounds I'h, I'i and I'j.

Scheme VI provides a procedure for preparation of diglycolic and thioglycolic acid mono esters of compounds of the formula I'. Everninomicin (10) is treated with excess, e.g., 2.5 equivalents of 60 (X=O or S) in the presence of 1 equivalent of DMAP and 8 equivalents of pyridine in methylene chloride at room temperature. The reaction mixture was stirred for 18 hours to give a mixture of the diglycolic or thioglycolic acid monoesters of formulas I'k ($R^3$=COCH$_2$SCH$_2$CO$_2$H and $R^6$=$R^7$=$R^8$=$R^1$=H) and I'l ($R^6$=COCH$_2$SCH$_2$CO$_2$H and $R^1$=$R^3$=$R^7$=$R^8$=H), I'm ($R^3$=COCH$_2$OCH$_2$CO$_2$H and $R^6$=$R^7$=$R^8$=$R^1$=H) and I'n ($R^6$=COCH$_2$OCH$_2$CO$_2$H and $R^1$=$R^3$=$R^7$=$R^8$=H). Each mixture of the diglycolic or thioglycolic acid monoesters was separated on silica gel using 10% methanol in methylene chloride. Separate treatment of each of the pure I'k ,I'l, I'm and I'n with 2 to 4 equivalents of base, e.g., NMG gave the corresponding amine salts.

Scheme VII provides a procedure for preparation of the polyether esters of the compounds of formula I', i.e. I'o wherein $R^3$=COCH$_2$O(CH$_2$CH$_2$O)$_n$CH$_3$ and $R^1$=$R^6$=$R^7$=$R^8$=H and I'p wherein $R^6$=COCH$_2$O(CH$_2$CH$_2$O)$_n$CH$_3$ and $R^1$=$R^3$=$R^7$=$R^8$=H; n=50–5000 for each. Compound 70 is treated with chloroacetic acid, sodium salt in the presence of NaH in THF to give 72. Treatment of 10 with 1 equivalent of 72 in methylene chloride in the presence of 1.3–1.5 equivalents of DCC and excess DMAP gives a mixture of I'o and I'p. Separation of the mixture on silica gel chromatography gives pure I'o and I'p.

The compounds of formula I of the invention are converted in vivo to everninomicin. Everninomicin is a known antibacterial agent (See International Patent Application, WO 93/07904 published Apr. 29, 1993 and U.S. Pat. No. 4,597,968).

The everninomicin, the compound of formula I' (compound 10 of Scheme I) may be obtained by fermentation of *Micromonospora carbonacea* var. africana NRRL 15099 ATCC 39149 or, more preferably, by an improved strain thereof, obtained as described in WO 93/07904 published Apr. 29, 1993.

The compounds of formula I' of the invention are converted in vivo everninomicin. Everninomicin is a known antibacterial agent (See International Publication No. WO 93/07904 published Apr. 29, 1993 and U.S. Pat. No. 4,597, 968). Accordingly, the compounds of formula I of the invention have antibacterial activity. Moreover, the compounds of formula I' of the invention are water soluble(i.e. have a solubility in aqueous medium of up to about 200 mg/ml) and therefore are conveniently formulated into aqueous solutions which are suitable for intravenous and intramuscular administration.

Following intravenous (IV) and intramuscular(IM) administration of various compounds of formula I' of the invention to mice, rats and monkeys; high serum levels of everninomicin, the compound of formula I', as shown in the Table hereinbelow:

| ANIMAL MODEL | A DOSE (mg/kg) | DOSING ROUTE | AUC[1] (μg.hr/ml) | $c_{max}$[2] (μg/ml) | $T_{max}$[3] (hr) |
|---|---|---|---|---|---|
| Mice | 10 | IV[4] | 29.3 | 19.9 | 0.25 |
|  | 10 | IM[5] | 29.7–49.5 | 11.3–29.9 | 0.25–2.00 |
| Monkeys | 10 | IV | 265 | 25.3 | 0.5 |
|  | 10 | IM | 255 | 29.9 | 1.0 |
| Rats | 60 | IV | 93.2 | 9.2 | 4.0 |
|  | 60 | IM | 163 | 25.6 | 1.0 |

[1] Area Under the Curve measured after 4 hours
[2] Maximum concentration
[3] Time of maximum concentration
[4] Intravenous
[5] Intramuscular The in vitro anti bacterial activity tests of everninomicin were performed via conventional agar dilution methods in Mueller-Hinton agar. The GMMs for everninomicin were determined against various bacteria, e.g. gram positive and gram negative bacteria. The term "susceptible gram positive and gram negative bacterial infections" means a broad range of gram positive bacterial infections, e.g. methicillin-resistant and methicillin-susceptible staphylococci, various strains of streptococci and enterococci and some gram negative bacterial infections, e.g., *E.coli, Klebsiella salmonella* and Pseudomonas. Everninomicin had excellent activity (10-fold more potent than vancomycin) against both methicillin-resistant staphylococci, (GMM, 0.1 μg/ml) and methicillin-susceptible staphylococci (GMM, 0.5 μg/ml). Everninomicin also had good activity (2-fold more potent than vancomycin against *Enterococcus faecalis* (GMM, 0.49 μg/ml) and good activity (MICs.≦0.5 μg/ml against various strains of streptococci and enterococci resistant to vancomycin (MICs≧128 μg/ml). Everninomicin was very active against *Borrelia burgdorferi* (MICs≦0.49 μg/ml) *Legionella pneumophila* and *L. longbeachea* (MICs≧2.5 μg/ml) but was only slightly active against gram negative bacteria (GMM≧760 μg/ml) *Trichiomonas vaginalis* (MICs≧192 μg/ml) and Mycoplasma (MICs≧200 μg/ml). No cross resistance with other antibiotics was observed.

Based upon the above data, the pharmaceutically acceptable compositions of the compounds of formula I are expected to be active against the above-listed susceptible bacteria as well as against spirochetes including Treponema paalidum anaerobes *Clostridium difficile* as well as against pneumocystis Toxoplasmas protozoa and helminths.

Based on the activity of everninomicin B, i.e the compound of formula 10, against *Borrelia burgdorferi* and *Legionella pneumophila* and *L. longbeachea* we expect that compounds of formula I will exhibit activity in a human model against Lyme disease and legionnaires disease.

The present invention provides a method of treating or preventing susceptible gram-positive and gram-negative infections in animals by administering to such animals especially man afflicted with such infections an amount of a compounds of formula I of the invention and a pharmaceutical carrier therefor.

The compositions of this invention may be prepared by admixing compounds of formula I of this invention with any pharmaceutically acceptable carrier, e.g. sterilized water, aqueous ethanol, vegetable oils or polyols eg. polythylene glycols and propylene glycol and administered orally, parenterally or topically in a variety of formulations. The use of sterilized ware as a carrier is preferred. The sterilized water may optionally contain pharmaceutically acceptable substances e.g. sodium chloride, potassium nitrate, glucose, mannitol dextrose, sorbitol or a buffer such as phosphate, acetate, or citrate as well as preservatives.

33

The bases found suitable for use in the present invention are those which form pharmaceutically acceptable salts of the compounds of formula I and include suitable organic and inorganic bases. Suitable organic bases include primary, secondary and tertiary alkyl amines, alkanolamines, aromatic amines, alkylaromatic amines, and cyclic amines. Exemplary organic amines include the pharmaceutically acceptable bases selected from the group consisting of chloroprocaine, procaine, piperazine, glucamine, N-methylglucamine, N, N-dimethylglucamine, ethylenediamine, dithanolamine, diisopropylamine, diethlamine, N-benzyl-2-phenylethylamine, N,N'-dibenzylethylenediamine, choline, clemizole, tris(hydroxymethyl)aminomethane, D-glucosamine, and morpholine, N-ethyl morpholine and N-methyl morpholine. The preferred organic bases include NMG N-methyl glucamine, diethanolamine, and tris(hydroxymethyl) aminomethane(TRIS). Use of NMG in this invention is most preferred. Mono to tetra NMG salts can be employed. Di-NMG salts are most preferred.

The suitable inorganic bases include alkali metal hydroxides such as sodium hydroxide.

The compounds of formula I of the invention have groups which are convertible in vivo into hydrogen The preferred compounds of formula I' of the invention contain one one to five groups, more preferably one group, convertible in vivo into hydrogen and have a solubility in aqueous medium of up to about 1 to 200 mg/ml.

For oral administration, the compositions of this invention may be compounded in the form of tablets, capsules elixirs or the like. Tablets and capsules may contain such excipients as starch or lactose; liquid forms may contain coloring or flavoring agents. Topical preparations may be in the form of creams hydrophobic and hydrophilic ointments or aqueous or non-aqueous or emulsion-type lotions as well as pessaries or powders. Typical carriers for such formulations are water, oils, grease, polyesters and polyols. Parenteral formulations e.g. injectible dosage forms are usually liquids such as solutions or suspensions with typical carriers being distilled water and saline. Parenteral formulations are preferred Intravenous formulations are more preferred.

The dose to be administered in any particular dosage form will depend upon various factors such as the weight, age and sex of the animal especially a mammal such as a human being who is being treated, the susceptibility of the infecting organism to the lipophilic oligosaccharide antibiotic, the stage and the severity of the infection. Generally, the dosage of the compounds of the invention of formula I' administered is from about 1.0 mg to about 15 mg per kilogram of body weight preferably 5 mg per kilogram of body weight per day in divided dosages, the specified dosage being left to the discretion of the practitioner; IV and intramuscular administration are preferred.

In treating certain patients with compositions of the invention, it is possible to include other pharmaceutically active ingredients in the same dosage unit.

SYNTHETIC EXAMPLES

General Experimental

The starting materials and reagents used to prepare the compounds of this invention are readily available from chemical suppliers e.g.; Sigma Chemical Company. Schemes I to VII illustrate the preparation of preferred compounds of this invention of formula I'. Standard synthetic chemical procedures well known to those skilled in the art may be employed to prepare the compounds of formula I' of this invention.

What is claimed is:

1. A method for preventing susceptible gram positive or gram negative bacterial infections in a mammal which comprises administering an antibacterial effective amount of a compound of of the formula I

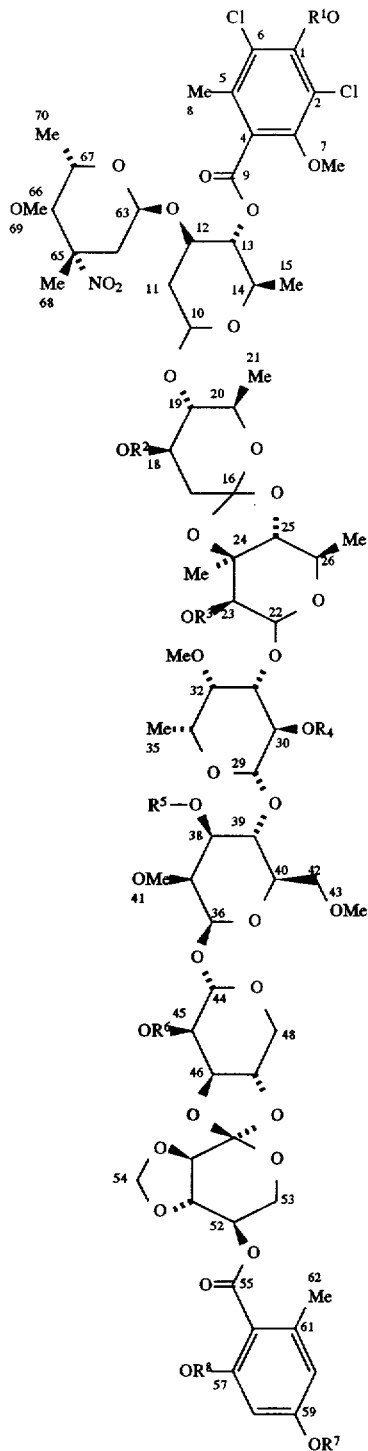

wherein one to seven of $R^1$, $R^2$, $R^3$, $R^4$, $R^5$, $R^6$, $R^7$, and $R^8$ are hydrogen and the remaining $R^1$, $R^2$, $R^3$, $R^4$, $R^5$, $R^6$, $R^7$, and $R^8$ are groups convertible in vivo into hydrogen or a pharmaceutically acceptable salt thereof.

2. A method according to claim 1 wherein the mode of administration is intravenous or intramuscular.

3. The method according to claim 2 wherein the compound is of the formula I'

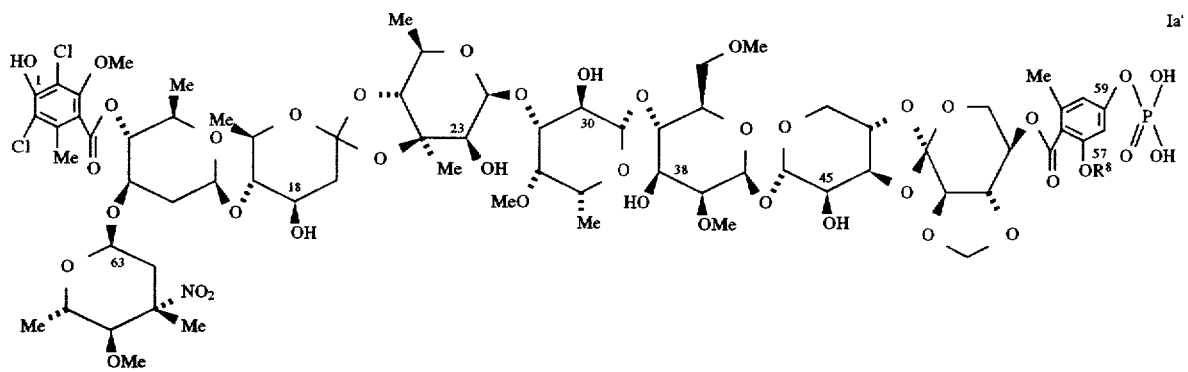

wherein one to four of $R^1$, $R^3$, $R^6$, $R^7$, and $R^8$ are hydrogen and the remaining $R^1$, $R^3$, $R^6$, $R^7$, and $R^8$ are groups convertible in vivo to hydrogen.

4. The method of claim 2 wherein the compound is of the formula I'

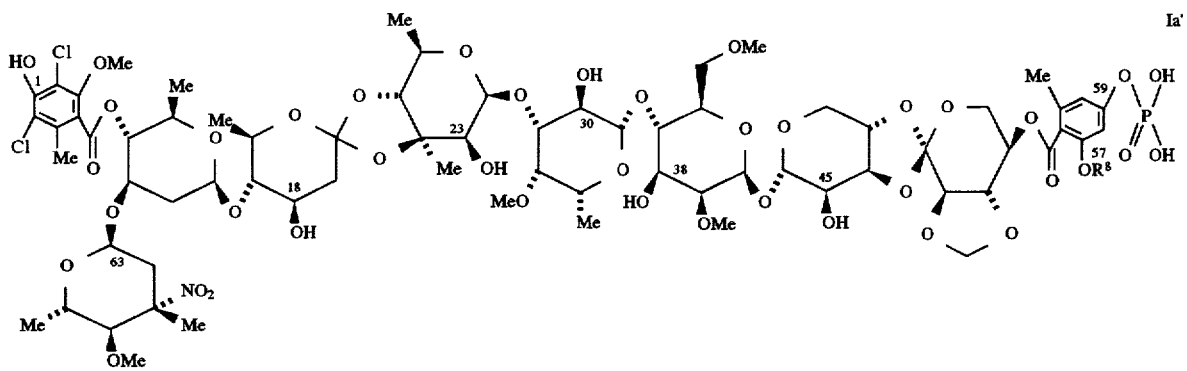

wherein one to four of $R^1$, $R^3$, $R^6$, $R^7$, and $R^8$ are hydrogen and the remaining $R^1$, $R^3$, $R^6$, $R^7$, and $R^8$ are each independently selected from the group consisting of

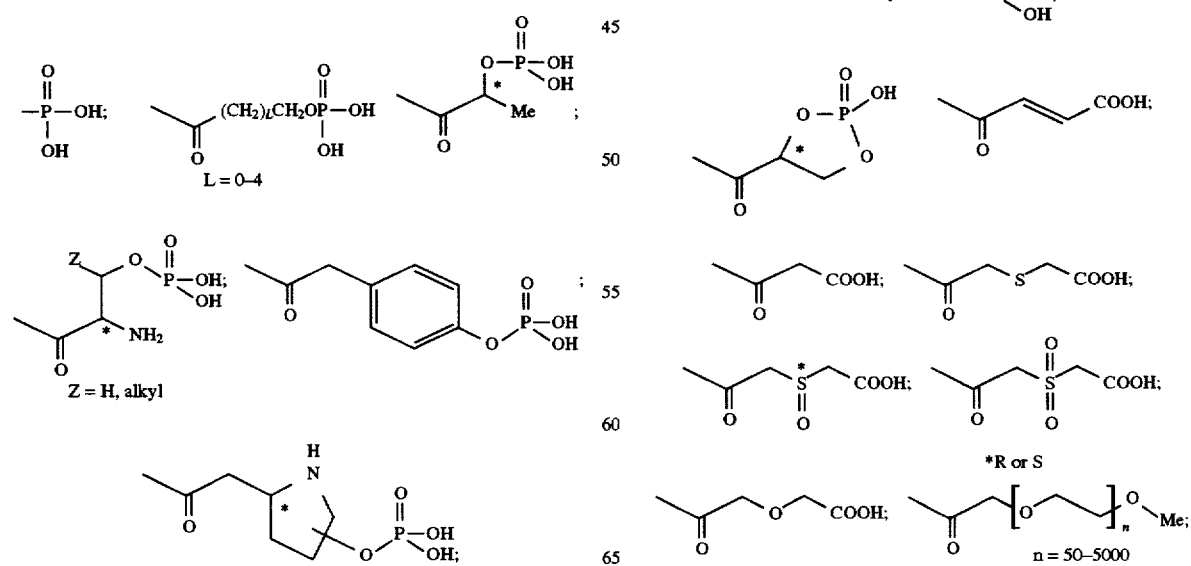

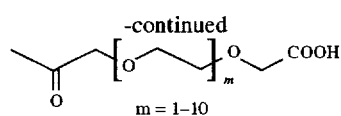
m = 1–10
or a pharmaceutically acceptable salt thereof.
5. The method of claim 2 wherein the compound is of the formula
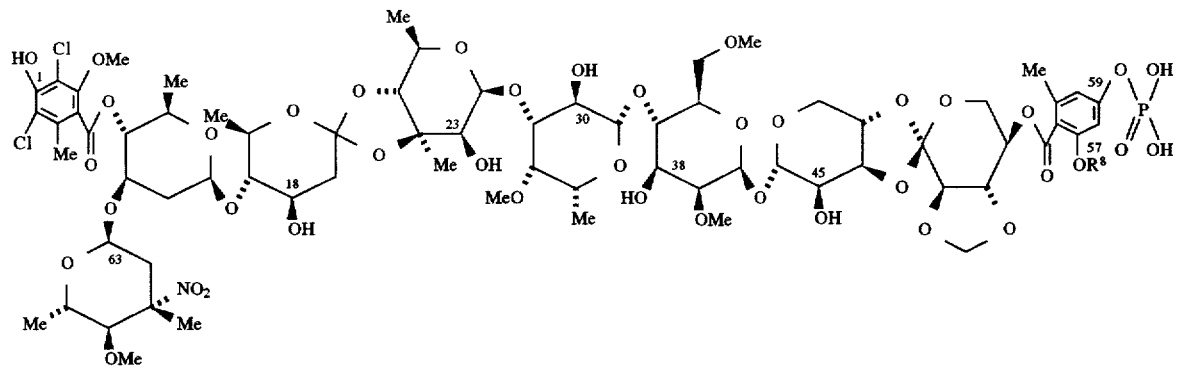
or a pharmaceutically acceptable salt thereof.
6. The method of claim 2 wherein the compound is of the formula
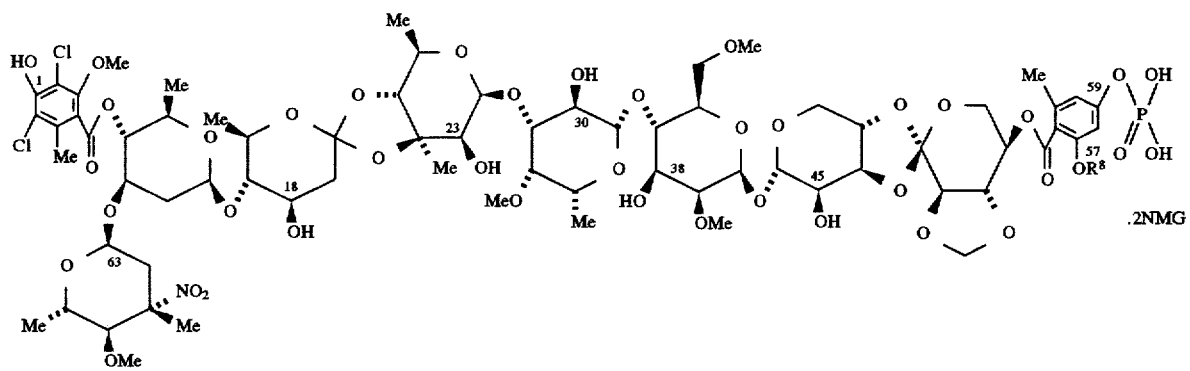
* * * * *